United States Patent [19]

Liu et al.

[11] 4,292,436
[45] Sep. 29, 1981

[54] PROCESS FOR THE PREPARATION OF N-PROTECTED N-FORMIMIDOYL 2-AMINOETHANETHIOL

[75] Inventors: Thomas M. H. Liu, Westfield; Robert A. Reamer, Bloomfield; Ichiro Shinkai, Westfield; Meyer Sletzinger, North Plainfield, all of N.J.

[73] Assignee: Merck & Co., Inc., Rahway, N.J.

[21] Appl. No.: 162,990

[22] Filed: Jun. 25, 1980

[51] Int. Cl.³ .................. C07C 149/20; C07C 125/06; C07F 7/10

[52] U.S. Cl. .................................. 560/148; 556/410; 564/102; 560/147

[58] Field of Search ........................ 556/410; 564/102; 560/147, 148

[56] References Cited

U.S. PATENT DOCUMENTS

| | | | |
|---|---|---|---|
| 3,531,524 | 9/1970 | Brown | 564/102 |
| 3,879,190 | 4/1975 | Fuchs | 560/147 X |
| 3,963,683 | 6/1976 | Gattuso | 564/102 X |
| 4,003,894 | 1/1977 | Verweij et al. | 556/410 X |

FOREIGN PATENT DOCUMENTS

| | | | |
|---|---|---|---|
| 1587 | 5/1979 | European Pat. Off. | 560/148 |
| 2137044 | 2/1973 | Fed. Rep. of Germany | 560/147 |
| 65922 | 3/1969 | German Democratic Rep. | 556/410 |

*Primary Examiner*—Paul F. Shaver
*Attorney, Agent, or Firm*—James A. Arno; Hesna J. Pfeiffer

[57] ABSTRACT

Disclosed is 2 and a process for its preparation:

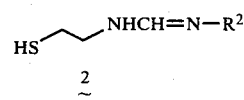

2

It is useful in the synthesis of N-formimidoyl thienamycin; $R^2$ is hydrogen or a protecting group.

8 Claims, No Drawings

PROCESS FOR THE PREPARATION OF N-PROTECTED N-FORMIMIDOYL 2-AMINOETHANETHIOL

BACKGROUND OF THE INVENTION

The antibiotic thienamycin is perhaps the best known member of the new family of antibiotics generically designated 1-carbapen-2-em-3-carboxylic acids. Derivatives of thienamycin, which were originally discovered on working with the natural product, are also well known. One of these, N-formimidoyl thienamycin (3), has been studied extensively:

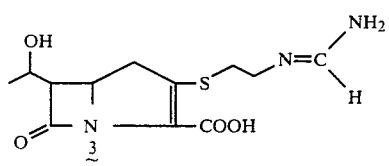

Because of the intrinsic instability of thienamycin, the preparation of 3 from thienamycin cannot be described as efficient since a variable but appreciable quantity of the starting thienamycin is lost in the process. The present invention relates to a process for the preparation of N-formimidoyl-2-aminoethanethiol and N-protected-N-formimidoyl-2-aminoethanethiols (2) which are useful in the preparation of N-formimidoyl thienamycin.

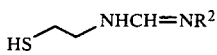

wherein $R^2$ is hydrogen or a protecting group.

The present invention also relates to a very efficient process for the direct synthesis of N-formimidoyl thienamycin (3) from the activated keto ester 1 on reaction with displacing agent 2 followed by hydrogenation:

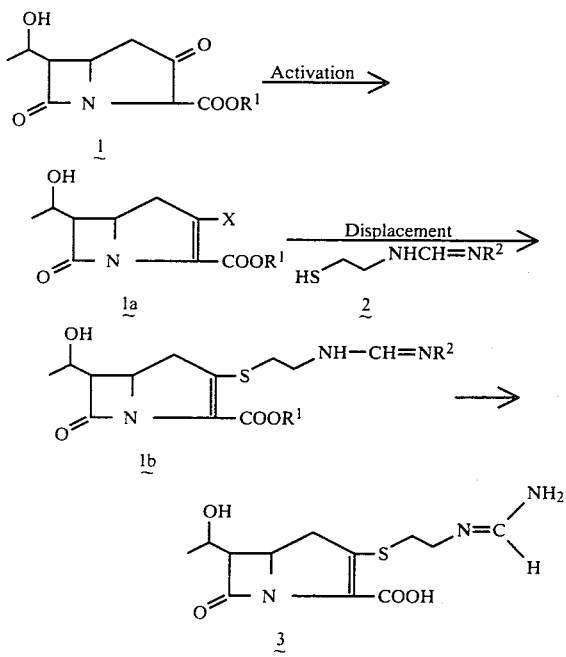

wherein $R^1$ and $R^2$ are protecting groups; and X is a leaving group. Details of this scheme, including preferred values for $R^1$ and $R^2$ are given below. It should be noted that step 1→1a is known; see European patent application No. 79101307.1 Publication No. 0007973/A1 (Feb. 20, 1980). Steps 1a→1b→3 are known in analogy to the synthesis of thienamycin and to that extent the cited European patent application is incorporated herein by reference.

DETAILED DESCRIPTION OF THE INVENTION

Reference is made to the foregoing reaction sequence 1→1a→1b→3 to conveniently describe the process of the present invention.

Activation of 1 to form 1a:

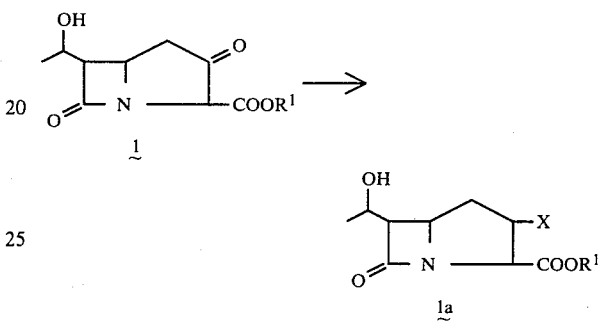

wherein X is a leaving group such as p-toluenesulfonyloxy, trifluoromethanesulfonate, diphenylphosphate or the like. As mentioned above, Step 1→1a is known. Typically, 1a is obtained by treating 1 in a solvent such as acetonitrile, dichloromethane, tetrahydrofuran (THF) or the like at a temperature of from −30° to 25° C. for from 0.5 to 2 hours with p-toluenesulfonic anhydride, trifluoromethanesulfonic anhydride, diphenylchlorophosphate or the like in the presence of a base such as diisopropylethylamine, triethylamine, pyridine or the like.

The transformation 1a→1b is accomplished by treating 1a in a solvent such as acetonitrile, N,N-dimethylformamide, dichloromethane, tetrahydrofuran or the like in the presence of a base such as diisopropylamine, triethylamine, pyridine or the like with displacing agent 2 wherein $R^2$ is a protecting group which is defined below. It should be noted that the total transformation 1→1b may be conducted as a "one-pot" single solvent transformation. Under such circumstances, the preferred leaving group X is selected from diphenylphosphate, trifluoromethane sulfonate or the like and the preferred solvent system is acetonitrile or dichloromethane at a temperature of from −20° to 0° C. for from 0.5 to 1 hour. Such one-pot, single solvent transformations are described for an analogous transformation in the synthesis of thienamycin. In this regard, co-pending commonly assigned U.S. patent application Ser. No. 144,015 filed Apr. 28, 1980 of Ichiro Shinkai is incorporated herein by reference.

The preparation of displacing agent 2 is described below. However, it should be noted that preferred values for protecting group $R^2$ are selected from the group consisting of p-nitrobenzyloxycarbonyl, phenylacetyl, triorganosilyl, such as trimethylsilyl and the like. The requirement of such protecting groups is that they permit the transformation 1b→3, which is discussed below. However, $R^2$ may be hydrogen. It should be noted that carboxyl protecting group $R^1$ may be any of the well known, readily removable carboxyl protecting groups; especially preferred values for $R^1$ include benzyl, p-nitrobenzyl, methoxymethyl and the like.

The final deblocking step $\underline{1b} \rightarrow \underline{3}$ is preferably accomplished by catalytic hydrogenation. Typically a catalyst such as platinum oxide, Pd/c, Pd(OH)$_2$, Pt/C or the like is employed with a hydrogen pressure of from 1 to 10 atmospheres at 0° to 25° C. Typically, under such conditions, $\underline{1b}$ in a solvent such as THF, dioxane, water or the like is subjected to the hydrogenation for from 0.5 to 12 hours to yield $\underline{3}$.

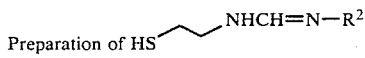
Preparation of

Preparation of the displacing agent $\underline{2}$ may conveniently be described by the following sequence:

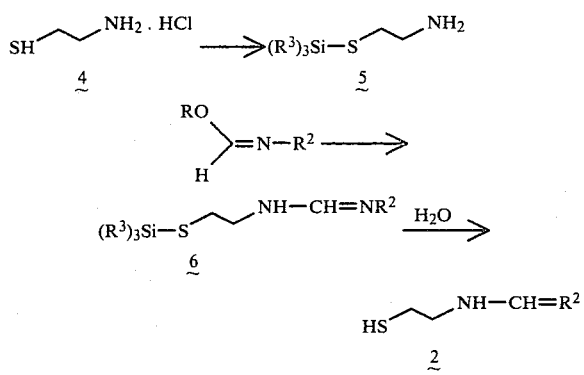

The reaction $\underline{4} \rightarrow \underline{5}$ is accomplished by treating 2-aminoethanethiol, preferably as its acid addition salt, such as the hydrochloride, hydrobromide, sulfate, perchlorate or the like, in a solvent such as acetonitrile, dichloromethane, THF, DMF or the like in the presence of 2 to 3 equivalents of a base such as diisopropylethylamine, triethylamine pyridine or the like with 1 to 1.5 equivalents of a triorganosilylating agent such as trimethylchlorosilane, t-butyldimethylchlorosilane, dimethylphenylchlorosilane or the like. It will be noted that there is no criticality as to the precise identity of the base in this reaction system. Likewise, there is no criticality as to the precise identity of the solvent, any solvent being suitable which permits the intended course of reaction. Further, it should be noted that while triloweralkylsilyl protecting groups are preferred, the requirement here is simply that the silyl function be successfully established and removed consistent with the overall production of the ultimately desired product $\underline{2}$. Thus, groups $R^3$ are independently selected from alkyl having from 1-6 carbon atoms, phenylalkyl having from 7-12 carbon atoms and phenyl. Other silylating agents, besides the chlorosilane, which are known to be equivalent are also suitable for the transformation $\underline{4} \rightarrow \underline{5}$.

The reaction $\underline{5} \rightarrow \underline{6}$ is accomplished by treating $\underline{5}$ in a solvent such as acetonitrile, DMF, THF or the like in the presence of a base such as diisopropylethylamine, triethylamine or the like with

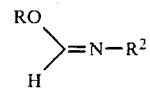

wherein R is alkyl having 1-6 carbon atoms, or aralkyl having 7-12 carbon atoms; and wherein $R^2$ is a protecting group such as p-nitrobenzyloxycarbonyl, phenylacetyl, phenoxyacetyl, trimethylsilyl or the like; especially preferred values for $R^2$ include p-nitrobenzyloxycarbonyl, and trimethylsilyl.

The transformation $\underline{6} \rightarrow \underline{2}$ is accomplished by treating $\underline{6}$ in a solvent such as acetonitrile, THF, DMF or the like at a temperature of from 0° to 25° C. with dilute aqueous acid or a catalytic amount of tetraalkyl ammonium fluoride. Desired reagent $\underline{2}$ may be isolated or it may be maintained in a solvent such as acetonitrile, THF (tetrahydrofuran), DMF(N,N-dimethylformamide) or the like for use in the above described process for the preparation of $\underline{3}$.

In the foregoing word description, it is to be understood that there is considerable latitude in selection of precise reaction parameters. Suggestion of this latitude and its breadth is generally indicated by enumeration of equivalent solvent systems, temperature ranges, protecting groups, and range of identities of involved reagents. Further, it is to be understood that the presentation of the synthetic scheme as comprising distinct steps in a given sequence is more in the nature of a descriptive convenience than as a necessary requirement; for one will recognize that the mechanically dissected scheme represents a unified scheme of synthesis and that certain steps, in actual practice, are capable of being merged, conducted simultaneously, or effected in a reverse sequence without materially altering the progress of synthesis.

The following examples recite a precise scheme. It is to be understood that the purpose of this recitation is to further illustrate the claimed process and not to impose any limitations. All temperatures are in °C.

EXAMPLE 1

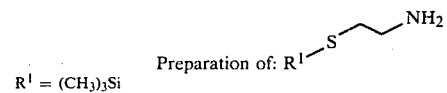

To a suspension of 2-aminoethanethiol hydrochloride (1.14 g, 10 mmol) in acetonitrile (15 ml) is added a solution of diisopropylethylamine (2.96 g, 3.99 ml, d=0.742, 23 mmol) in acetonitrile (1 containing a catalytic amount (1-2 mg) of imidazole at 0° C. under a nitrogen atmosphere. A solution of trimethylchlorosilane (1.41 g, 1.64 ml, d=0.856, 13 mmol) in acetonitrile (1.0 ml) is slowly added (over 2 min) to the above solution. The resulting mixture is then allowed to warm up to room temperature for 15 min and then cooled again to 0° C. This solution of $\underline{4}$ is conveniently held for later use.

EXAMPLE 2

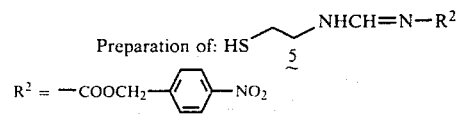

To a solution of isopropylformimidate hydrochloride (0.71 g, 5.7 mmol) in acetonitrile (10 ml) is slowly added diisopropylethylamine (1.5 g, 2.02 ml d=0.742, 11.6 mmol) at 0° C. under a nitrogen atmosphere. To the resulting solution is added a solution of p-nitrobenzylchloroformate (1.23 g, 5.7 mmol) in acetonitrile (2 ml) at 0° C. The resulting clear solution is designated Solution A.

To Solution A is added one-half of the solution comprising 4 from Example 1. The resulting mixture is stirred for 10 min at room temperature; whereupon water (2.0 ml) is added. The solvent is evaporated in vacuo, and the residue is dissolved in dichloromethane (20 ml) and washed with water (3×20 ml). The extract is dried over sodium sulfate and the solvent is evaporated in vacuo to give crude N-(N-p-nitrobenzyloxycarbonyl)-formimidoyl-2-aminoethanethiol (5); yield: 1.13 g (79.6%).

The crude material 5 is purified by a short column of silica gel (20 g of $SiO_2$). Elution with ethylacetate gave pure 5; 10 mg (50% yield); tlc $SiO_2$-ethylacetate $R_f=0.35$, mass spectrum=m/e=283 (M+),

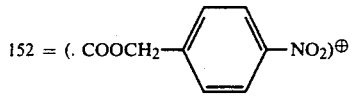

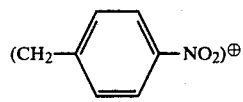

C—NMR=DMSO-$d_6$(internal TMS, $\delta_c=0.0$ppm) 22.6(—$CH_2SH$), 44.0(—$NCH_2$—), 65.1(—$OCH_2$—), 123.5(Aromatic $C_{3,5}$), 128.3 (Aromatic $C_{2,6}$), 145.2 (aromatic $C_1$), 146.9 (Ar—$C_4$), 161.0 (NH—CH=N—, $J_{CH}=178.2$ Hz), 163.7 ($NCO_2$).

EXAMPLE 3

Following the procedure of Example 2, except substituting an equivalent amount of:

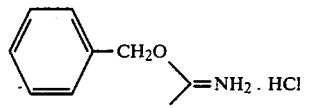

984 mg(5.7 mmol)

for the isopropyl formimidate hydrochloride there is obtained 5; yield 790 mg (56%) based on 2-aminoethanethiol.

EXAMPLE 4

Preparation of 1b

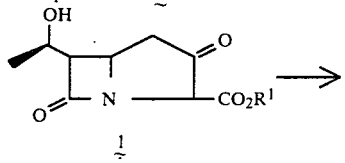

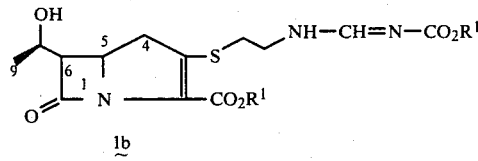

To a solution of the bicyclic keto ester 1 (300 mg, 0.86 mmol) in acetonitrile (2 ml) is added dropwise diisopropylethylamine (130 ml, 1 mmol) at 0° C. under nitrogen atmosphere over 2 min. After the resulting mixture is stirred for 5 min at 0° C., a solution of diphenylchlorophosphate (265 mg, 1 mmol) and diisopropylethylamine (130 mg, 1 mmol) in acetonitrile (2 ml) is added dropwise to the above mixture. The mixture is stirred for 10 min at 0° C. and then for an additional 15 min at room temperature. To the above solution is added a solution of N-(N-p-nitrobenzyloxycarbonyl)formimidoyl-2-aminoethanethiol (243 mg, 0.86 mmol) in acetonitrile (1 ml) at 0° C. The mixture is stirred for 2 hrs. at the same temperature, poured into ice-water (200 ml), and extracted with dichloromethane (3×20 ml). The combined extracts are washed with water (2×10 ml), and dried over sodium sulfate. Evaporation of the solvent in vacuo gives crude 1b. $^{13}$C—NMR (acetone-$d_6$, internal TMS $\delta=0.0$ ppm) 22.2 ($C_9$) 31.2 ($SCH_2$), 40.8, 42.2 ($NCH_2$ and $C_4$), 53.5 ($C_5$), 65.4, 66.2 (2×—$OCH_2$—), 65.7 ($C_6$), 67.9 ($C_8$) 124.3 ($C_2$ & 2×$ArC_3$, $C_5'$), 129.0, 129.1, (2×$ArC_2'_6'$) 145.1, 146.2 (2×Ar $C_1'$), 148.4 (2×$ArC_4'$), 150.2 ($C_3$), 161.4 ($CO_2R$), 162.3 (NH—CH=N) 164.7 (—$NCO_2$), 177.6 ($C_7$).

$^1$H NMR (acetone-$d_6$, internal TMS $\delta=0.0$ ppm) 1.23 (s,$CH_3$), 3.2(m, $SCH_2$), 3.36 (d of d, 6-H), centered at 3.58 (ABX, 4-$CH_2$), 3.7(m, $NCH_2$), 4.14(m, 8-H), 4.34 (m, 5-H), 5.3 (s, $OCH_2$), centered at 5.44 (AB, $OCH_2$), 8.62 (bs, N=CH—), 8 aromatic CH's.

EXAMPLE 5

Preparation of 3:

A solution of bis-protected 3 (1b from Example 4) (20 mg, 0.033 mmol), tetrahydrofuran (2.0 ml), 0.5 M morpholinopropanesulfonic acid (adjusted to pH 7.0 by adding sodium hydroxide; 0.5 ml) and water (2 ml) is hydrogenated over platinum oxide (20 mg) under 40 psi hydrogen pressure for 45 min. The catalyst is filtered and washed with water. The filtrate is washed with ethylacetate to remove organic impurities. The water layer is diluted to 50 ml and assayed by HPLC indicated that this solution contains 116/ml of 3, which is a 59% yield.

HPLC conditions
col.=MC-18 10μ
microporous C-18 bonded phase column
eluent=0.05 M phosphate buffer at pH 7.0
detection=UV 300 nm
retention time~500 sec.

EXAMPLE 6

Preparation of 3:

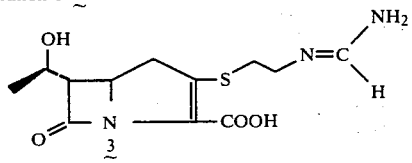

A solution of bisprotected N-formimidoyl thienamycin 1b (Example 4; 200 mg, 0.33 mmol), THF (3 ml), 0.5 M MOPS (0.5 ml), and water (2 ml) is hydrogenated over platinum oxide (50 mg) under 40 psi hydrogen pressure for 40 min. After the usual work up, the crude product 3 is purified by column of Dowex-50 to give crystalline 3, 34.1 mg (35% yield).

What is claimed is:

1. A compound of the formula:

wherein $R^2$ is hydrogen or a protecting group is selected from the group consisting of: triorganosilyl,

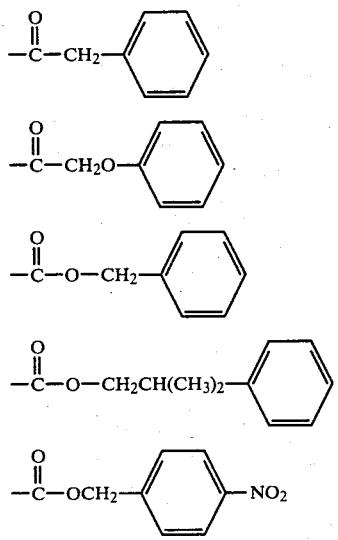

2. A compound according to claim 1 wherein the triorganosilyl is $(R^3)_3Si-$ and $R^3$ is independently selected from alkyl having 1-6 carbon atoms, phenyl and phenylalkyl having 7-12 carbon atoms.

3. A process for preparing:

comprising the steps of treating 2-aminoethanethiol in the presence of base with a silylating agent followed by treating with:

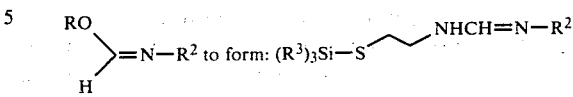

followed by hydrolysis: wherein $R^2$ is a readily removable N-protecting group; $R^3$ is independently chosen from alkyl having from 1-6 carbon atoms, phenyl and phenylalkyl having from 7-12 carbon atoms; and RO— is a leaving group.

4. A process according to claim 3 wherein $R^2$ is selected from the group consisting of:

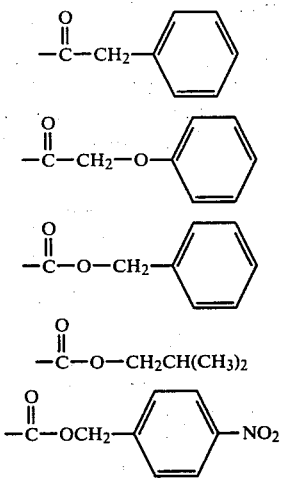

—Si(CH$_3$)$_3$; and
R is alkyl having 1-6 carbon atoms, or aralkyl having 7-12 carbon atoms.

5. A process according to claim 3 or 4 wherein $(R^3)_3Si-$ represents a trialkylsilyl group.

6. A process according to claim 5 wherein the trialkylsilyl is selected from the group consisting of:
—Si(CH$_3$)$_3$
—Si(CH$_3$)$_2$[C(CH$_3$)$_3$]
—Si(CH$_3$)$_2$(CH$_2$CH$_3$)
—Si(CH$_3$)$_2$(CH$_2$C$_6$H$_5$)

7. A compound according to claim 1 wherein $R^2$ is selected from the group consisting of:
—Si(CH$_3$)$_3$
—Si(CH$_3$)$_2$[C(CH$_3$)$_3$]
—Si(CH$_3$)$_2$(CH$_2$CH$_3$)
—Si(CH$_3$)$_2$(CH$_2$C$_6$H$_5$)

8. A compound according to claim 1 wherein $R^2$ is

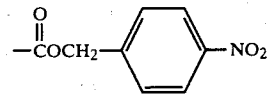

* * * * *